(12) United States Patent
Connolly et al.

(10) Patent No.: US 7,587,287 B2
(45) Date of Patent: Sep. 8, 2009

(54) METHOD AND SYSTEM FOR TRANSFERRING ANALYTE TEST DATA

(75) Inventors: Brian Edmond Connolly, Reading, MA (US); Chad Harold Mace, Hudson, NH (US); Marc R. Lai, Dover, MA (US)

(73) Assignee: Abbott Diabetes Care Inc., Alameda, CA (US)

( * ) Notice: Subject to any disclaimer, the term of this patent is extended or adjusted under 35 U.S.C. 154(b) by 107 days.

(21) Appl. No.: 10/407,695

(22) Filed: Apr. 4, 2003

(65) Prior Publication Data

US 2004/0249999 A1 Dec. 9, 2004

(51) Int. Cl.
*G01N 31/00* (2006.01)

(52) U.S. Cl. ........................................................ 702/32
(58) Field of Classification Search .................... 702/32; 600/300; 455/569.2
See application file for complete search history.

(56) References Cited

U.S. PATENT DOCUMENTS

| | | | |
|---|---|---|---|
| 3,304,413 A | 2/1967 | Lehmann et al. |
| 3,651,318 A | 3/1972 | Czekajewski |
| 3,698,386 A | 10/1972 | Fried |
| 3,768,014 A | 10/1973 | Smith et al. |
| 3,919,051 A | 11/1975 | Koch et al. |
| 4,154,231 A | 5/1979 | Russell |
| 4,240,889 A | 12/1980 | Yoda et al. |
| 4,271,449 A | 6/1981 | Grogan |
| 4,318,784 A | 3/1982 | Higgins et al. |
| 4,331,869 A | 5/1982 | Rollo |
| 4,392,933 A | 7/1983 | Nakamura et al. |
| 4,397,956 A | 8/1983 | Maggio |
| 4,407,959 A | 10/1983 | Tsuji et al. |
| 4,417,588 A | 11/1983 | Houghton et al. |
| 4,420,564 A | 12/1983 | Tsuji et al. |
| 4,444,892 A | 4/1984 | Malmros |

(Continued)

FOREIGN PATENT DOCUMENTS

DE 42 34 553 C2 1/1995

(Continued)

OTHER PUBLICATIONS

Supplemental European Search Report for European Patent Application No. 04749713.6 filed Apr. 2, 2004, mailed Mar. 5, 2009.

*Primary Examiner*—Tung S Lau
*Assistant Examiner*—Xiuquin Sun
(74) *Attorney, Agent, or Firm*—Jackson & Co., LLP

(57) ABSTRACT

A system for transferring data includes an analyte test instrument (ATI) adapted to store data, a wirelessly enabled data management device (DMD) for comprehensively analyzing data, and an adaptor removably connected to the ATI for transferring data stored on the ATI to the DMD. The adaptor includes a data communication device capable of removable connection with the ATI, a microprocessor electrically connected to the data communication device, a wireless controller electrically connected to the microprocessor and a wireless transceiver electrically connected to the wireless controller. In use, data transfer is executed between the ATI and the DMD by electrically and mechanically connecting the adaptor to the ATI. Data stored on the ATI is then automatically downloaded into adaptor memory. Upon completion of the download, the user activates an externally accessible input device on the adaptor which, in turn, wirelessly transmits data from the adaptor memory to the DMD.

19 Claims, 7 Drawing Sheets

U.S. PATENT DOCUMENTS

| | | | |
|---|---|---|---|
| 4,483,924 A | 11/1984 | Tsuji et al. |
| 4,569,589 A | 2/1986 | Neufeld |
| 4,595,479 A | 6/1986 | Kimura et al. |
| 4,633,881 A | 1/1987 | Moore et al. |
| 4,648,408 A | 3/1987 | Hutcheson et al. |
| 4,653,513 A | 3/1987 | Dombrowski |
| 4,674,652 A | 6/1987 | Aten et al. |
| 4,686,624 A | 8/1987 | Blum et al. |
| 4,731,726 A | 3/1988 | Allen, III |
| 4,750,496 A | 6/1988 | Reinhardt |
| 4,803,625 A | 2/1989 | Fu et al. |
| 4,835,372 A | 5/1989 | Gombrich et al. |
| RE32,974 E | 7/1989 | Porat et al. |
| 4,857,713 A | 8/1989 | Brown |
| 4,858,617 A | 8/1989 | Sanders |
| 4,870,561 A | 9/1989 | Love et al. |
| 4,874,499 A | 10/1989 | Smith et al. |
| 4,899,839 A | 2/1990 | Dessertine et al. |
| 4,920,969 A | 5/1990 | Suzuki |
| 4,920,977 A | 5/1990 | Haynes |
| 4,936,956 A | 6/1990 | Wrighton |
| 4,942,127 A | 7/1990 | Wada et al. |
| 4,945,045 A | 7/1990 | Forrest et al. |
| 4,957,115 A | 9/1990 | Selker |
| 4,958,632 A | 9/1990 | Duggan |
| 4,968,400 A | 11/1990 | Shimomura et al. |
| 4,994,068 A | 2/1991 | Hufnagle |
| 5,007,427 A | 4/1991 | Suzuki et al. |
| 5,016,172 A | 5/1991 | Dessertine |
| 5,019,974 A | 5/1991 | Beckers |
| 5,034,192 A | 7/1991 | Wrighton et al. |
| 5,037,527 A | 8/1991 | Hayashi et al. |
| 5,049,487 A | 9/1991 | Phillips et al. |
| 5,068,536 A | 11/1991 | Rosenthal |
| 5,073,500 A | 12/1991 | Saito et al. |
| 5,075,792 A | 12/1991 | Brown et al. |
| 5,077,476 A | 12/1991 | Rosenthal |
| 5,078,854 A | 1/1992 | Burgess et al. |
| 5,084,828 A | 1/1992 | Kaufman et al. |
| 5,094,951 A | 3/1992 | Rosenberg |
| 5,096,560 A | 3/1992 | Takai et al. |
| 5,096,836 A | 3/1992 | Macho et al. |
| 5,111,539 A | 5/1992 | Hiruta et al. |
| 5,111,818 A | 5/1992 | Suzuji et al. |
| 5,114,678 A | 5/1992 | Crawford et al. |
| 5,120,421 A | 6/1992 | Glass et al. |
| 5,126,247 A | 6/1992 | Palmer et al. |
| 5,130,009 A | 7/1992 | Marsoner et al. |
| 5,134,391 A | 7/1992 | Okada |
| 5,140,393 A | 8/1992 | Hijikihigawa et al. |
| 5,168,046 A | 12/1992 | Hamamoto et al. |
| 5,182,707 A | 1/1993 | Cooper et al. |
| 5,184,359 A | 2/1993 | Tsukamura et al. |
| 5,185,256 A | 2/1993 | Nankai et al. |
| 5,190,041 A | 3/1993 | Palti |
| 5,192,415 A | 3/1993 | Yoshioka et al. |
| 5,200,051 A | 4/1993 | Cozzette et al. |
| 5,204,532 A | 4/1993 | Rosenthal |
| 5,206,145 A | 4/1993 | Cattell |
| 5,216,597 A | 6/1993 | Beckers |
| 5,227,042 A | 7/1993 | Zawodzinski et al. |
| 5,251,126 A | 10/1993 | Kahn et al. |
| 5,261,401 A | 11/1993 | Baker et al. |
| 5,265,888 A | 11/1993 | Yamamoto et al. |
| 5,266,179 A | 11/1993 | Nankai et al. |
| 5,269,212 A | 12/1993 | Peters et al. |
| 5,272,060 A | 12/1993 | Hamamoto et al. |
| 5,275,159 A | 1/1994 | Griebel |
| 5,278,079 A | 1/1994 | Gubinski et al. |
| 5,279,294 A | 1/1994 | Anderson |
| 5,282,950 A | 2/1994 | Dietze et al. |
| 5,304,468 A | 4/1994 | Phillips et al. |
| 5,307,263 A | 4/1994 | Brown |
| 5,309,919 A | 5/1994 | Snell et al. |
| 5,310,885 A | 5/1994 | Maier et al. |
| 5,317,691 A | 5/1994 | Traeger |
| 5,324,303 A | 6/1994 | Strong et al. |
| 5,326,449 A | 7/1994 | Cunningham |
| 5,337,258 A | 8/1994 | Dennis |
| 5,364,797 A | 11/1994 | Olson et al. |
| 5,366,609 A | 11/1994 | White et al. |
| 5,376,251 A | 12/1994 | Kaneko et al. |
| 5,377,258 A | 12/1994 | Bro |
| 5,380,422 A | 1/1995 | Negishi et al. |
| 5,382,346 A | 1/1995 | Uenoyama et al. |
| 5,393,903 A | 2/1995 | Gratzel et al. |
| 5,410,471 A | 4/1995 | Alyfuku et al. |
| 5,410,474 A | 4/1995 | Fox |
| 5,413,690 A | 5/1995 | Kost et al. |
| 5,417,222 A | 5/1995 | Dempsey et al. |
| 5,422,246 A | 6/1995 | Koopal et al. |
| 5,431,691 A | 7/1995 | Snell et al. |
| 5,437,973 A | 8/1995 | Vadgama et al. |
| 5,440,559 A | 8/1995 | Gaskill |
| 5,456,692 A | 10/1995 | Smith, Jr. et al. |
| 5,484,991 A | 1/1996 | Sherman et al. |
| 5,487,751 A | 1/1996 | Radons et al. |
| 5,501,956 A | 3/1996 | Wada et al. |
| 5,507,288 A | 4/1996 | Bocker et al. |
| 5,508,171 A | 4/1996 | Walling et al. |
| 5,514,253 A | 5/1996 | Davis et al. |
| 5,518,006 A | 5/1996 | Mawhirt et al. |
| 5,519,527 A | 5/1996 | Panton |
| 5,520,787 A | 5/1996 | Hanagan et al. |
| 5,525,511 A | 6/1996 | D'Costa |
| 5,526,120 A | 6/1996 | Jina et al. |
| 5,528,391 A | 6/1996 | Elrod |
| 5,549,113 A | 8/1996 | Halleck et al. |
| 5,549,115 A | 8/1996 | Morgan et al. |
| 5,552,027 A | 9/1996 | Birkle et al. |
| 5,554,166 A | 9/1996 | Lange et al. |
| 5,556,524 A | 9/1996 | Albers |
| 5,560,357 A | 10/1996 | Faupel et al. |
| 5,566,022 A | 10/1996 | Segev |
| 5,569,212 A | 10/1996 | Brown |
| 5,575,895 A | 11/1996 | Ikeda et al. |
| 5,580,527 A | 12/1996 | Bell et al. |
| 5,580,794 A | 12/1996 | Allen |
| 5,596,994 A | 1/1997 | Bro |
| 5,601,435 A | 2/1997 | Quy |
| 5,623,925 A | 4/1997 | Swenson et al. |
| 5,628,309 A | 5/1997 | Brown |
| 5,629,981 A | 5/1997 | Nerlikar |
| 5,636,264 A | 6/1997 | Sulavuori et al. |
| 5,643,212 A | 7/1997 | Coutre et al. |
| 5,650,062 A | 7/1997 | Ikeda et al. |
| 5,678,571 A | 10/1997 | Brown |
| 5,682,157 A | 10/1997 | Asmussen et al. |
| 5,686,717 A | 11/1997 | Knowles et al. |
| 5,695,949 A | 12/1997 | Galen et al. |
| 5,701,894 A | 12/1997 | Cherry et al. |
| 5,704,922 A | 1/1998 | Brown |
| 5,710,630 A | 1/1998 | Essenpreis et al. |
| 5,720,733 A | 2/1998 | Brown |
| 5,720,862 A | 2/1998 | Hamamoto et al. |
| 5,721,783 A | 2/1998 | Anderson |
| 5,724,168 A | 3/1998 | Oschmann et al. |
| 5,727,548 A | 3/1998 | Hill et al. |
| 5,730,124 A | 3/1998 | Yamauchi |
| 5,730,654 A | 3/1998 | Brown |
| 5,735,285 A | 4/1998 | Albert et al. |
| 5,741,688 A | 4/1998 | Oxenboll et al. |
| 5,746,217 A | 5/1998 | Erickson et al. |
| 5,757,277 A | 5/1998 | Kobayashi |

| | | | | | |
|---|---|---|---|---|---|
| 5,770,028 A | 6/1998 | Maley et al. | 6,088,730 A | 7/2000 | Kato et al. |
| 5,772,586 A | 6/1998 | Heinonen et al. | 6,093,156 A | 7/2000 | Cunningham et al. |
| 5,781,321 A | 7/1998 | Kobayashi | 6,097,831 A | 8/2000 | Wieck et al. |
| 5,782,814 A | 7/1998 | Brown et al. | 6,099,484 A | 8/2000 | Douglas et al. |
| 5,786,584 A | 7/1998 | Button et al. | 6,101,478 A | 8/2000 | Brown |
| 5,792,117 A | 8/1998 | Brown | 6,103,033 A | 8/2000 | Say et al. |
| 5,804,048 A | 9/1998 | Wong et al. | 6,106,780 A | 8/2000 | Douglas et al. |
| 5,820,570 A | 10/1998 | Erickson et al. | 6,110,148 A | 8/2000 | Brown et al. |
| 5,827,179 A | 10/1998 | Lichter et al. | 6,113,578 A | 9/2000 | Brown |
| 5,828,943 A | 10/1998 | Brown | 6,115,161 A | 9/2000 | Cho |
| 5,830,341 A | 11/1998 | Gilmartin | 6,120,676 A | 9/2000 | Heller et al. |
| 5,832,448 A | 11/1998 | Brown | 6,122,351 A | 9/2000 | Schlueter, Jr. et al. |
| 5,834,224 A | 11/1998 | Ruger et al. | 6,124,134 A | 9/2000 | Stark |
| 5,837,454 A | 11/1998 | Cozzette et al. | 6,134,504 A | 10/2000 | Douglas et al. |
| 5,837,546 A | 11/1998 | Allen et al. | 6,143,164 A | 11/2000 | Heller et al. |
| 5,840,020 A | 11/1998 | Heinonen et al. | 6,144,837 A | 11/2000 | Quy |
| 5,846,702 A | 12/1998 | Deng et al. | 6,144,922 A | 11/2000 | Douglas et al. |
| 5,846,744 A | 12/1998 | Athey et al. | 6,148,094 A | 11/2000 | Kinsella |
| 5,857,967 A | 1/1999 | Frid et al. | 6,151,586 A | 11/2000 | Brown |
| 5,857,983 A | 1/1999 | Douglas et al. | 6,153,062 A | 11/2000 | Saito et al. |
| 5,860,917 A | 1/1999 | Comanor et al. | 6,153,069 A | 11/2000 | Pottgen et al. |
| 5,861,968 A | 1/1999 | Kerklaan et al. | 6,159,147 A | 12/2000 | Lichter et al. |
| 5,872,713 A | 2/1999 | Douglas et al. | 6,161,095 A | 12/2000 | Brown |
| 5,873,990 A | 2/1999 | Wojciechowski et al. | 6,162,639 A | 12/2000 | Douglas |
| 5,877,880 A | 3/1999 | Kuo | 6,167,362 A | 12/2000 | Brown et al. |
| 5,879,163 A | 3/1999 | Brown et al. | 6,168,563 B1 | 1/2001 | Brown |
| 5,879,311 A | 3/1999 | Duchon et al. | 6,170,318 B1 | 1/2001 | Lewis et al. |
| 5,880,829 A | 3/1999 | Kauhaniemi et al. | 6,175,752 B1 | 1/2001 | Say et al. |
| 5,887,133 A | 3/1999 | Brown et al. | 6,186,145 B1 | 2/2001 | Brown |
| 5,897,493 A | 4/1999 | Brown | 6,192,891 B1 | 2/2001 | Gravel et al. |
| 5,899,855 A | 5/1999 | Brown | 6,193,873 B1 | 2/2001 | Ohara et al. |
| 5,903,373 A | 5/1999 | Welch et al. | D439,242 S | 3/2001 | Brown et al. |
| 5,903,374 A | 5/1999 | Kobayashi | 6,196,970 B1 | 3/2001 | Brown |
| 5,913,310 A | 6/1999 | Brown | 6,198,957 B1 | 3/2001 | Green |
| 5,918,603 A | 7/1999 | Brown | 6,206,841 B1 | 3/2001 | Cunningham |
| 5,925,021 A | 7/1999 | Castellano et al. | 6,210,272 B1 | 4/2001 | Brown |
| 5,929,771 A | 7/1999 | Gaskill | 6,219,565 B1 | 4/2001 | Cupp et al. |
| 5,931,791 A | 8/1999 | Saltzstein et al. | 6,233,539 B1 | 5/2001 | Brown |
| 5,933,136 A | 8/1999 | Brown | 6,236,486 B1 | 5/2001 | Nocker, IV |
| 5,940,801 A | 8/1999 | Brown | 6,241,862 B1 | 6/2001 | McAleer et al. |
| 5,942,979 A | 8/1999 | Luppino | 6,246,330 B1 | 6/2001 | Nielsen |
| 5,945,345 A | 8/1999 | Blatt et al. | 6,246,992 B1 | 6/2001 | Brown |
| 5,950,632 A | 9/1999 | Reber et al. | 6,248,065 B1 | 6/2001 | Brown |
| 5,951,300 A | 9/1999 | Brown | 6,248,067 B1 * | 6/2001 | Causey et al. ............... 600/365 |
| 5,951,492 A | 9/1999 | Douglas et al. | 6,251,260 B1 | 6/2001 | Heller et al. |
| 5,956,501 A | 9/1999 | Brown | 6,256,129 B1 | 7/2001 | Kim et al. |
| 5,960,403 A | 9/1999 | Brown | 6,256,643 B1 | 7/2001 | Cork et al. |
| 5,961,451 A | 10/1999 | Reber et al. | 6,260,022 B1 | 7/2001 | Brown |
| 5,968,839 A | 10/1999 | Blatt et al. | 6,266,645 B1 | 7/2001 | Simpson |
| 5,971,941 A | 10/1999 | Simons et al. | 6,270,445 B1 | 8/2001 | Dean, Jr. et al. |
| 5,974,124 A | 10/1999 | Schlueter, Jr. et al. | 6,281,006 B1 | 8/2001 | Heller et al. |
| 5,977,476 A | 11/1999 | Guha et al. | 6,281,999 B1 | 8/2001 | Watson et al. |
| 5,981,294 A | 11/1999 | Blatt et al. | 6,294,281 B1 | 9/2001 | Heller |
| 5,986,787 A | 11/1999 | Ohshima et al. | 6,295,506 B1 | 9/2001 | Heinonen et al. |
| 5,994,476 A | 11/1999 | Shin et al. | 6,299,757 B1 | 10/2001 | Feldman et al. |
| 5,997,476 A | 12/1999 | Brown | 6,301,035 B1 | 10/2001 | Schairer |
| 6,004,441 A | 12/1999 | Fujiwara et al. | 6,329,161 B1 | 12/2001 | Heller et al. |
| 6,008,923 A | 12/1999 | Samdahl et al. | 6,330,426 B2 | 12/2001 | Brown et al. |
| 6,024,699 A | 2/2000 | Surwit et al. | 6,334,778 B1 | 1/2002 | Brown |
| 6,027,459 A | 2/2000 | Shain et al. | 6,338,790 B1 | 1/2002 | Feldman et al. |
| 6,027,692 A | 2/2000 | Galen et al. | 6,377,894 B1 | 4/2002 | Deweese et al. |
| 6,032,199 A | 2/2000 | Brown et al. | 6,379,301 B1 | 4/2002 | Worthington et al. |
| 6,033,866 A | 3/2000 | Guo et al. | 6,442,637 B1 | 8/2002 | Hawkins et al. |
| D424,696 S | 5/2000 | Ray et al. | 6,442,639 B1 | 8/2002 | McElhattan et al. |
| 6,063,459 A | 5/2000 | Velte | 6,449,075 B1 | 9/2002 | Watson et al. |
| 6,066,243 A | 5/2000 | Anderson et al. | 6,494,830 B1 | 12/2002 | Wessel |
| 6,068,615 A | 5/2000 | Brown et al. | 6,516,359 B1 | 2/2003 | Kurihara et al. |
| D426,638 S | 6/2000 | Ray et al. | 6,558,320 B1 * | 5/2003 | Causey et al. ............... 600/300 |
| D427,312 S | 6/2000 | Douglas | 6,610,012 B2 | 8/2003 | Mault |
| 6,071,249 A | 6/2000 | Cunningham et al. | 6,633,772 B2 | 10/2003 | Ford et al. |
| 6,071,251 A | 6/2000 | Cunningham et al. | 6,641,533 B2 * | 11/2003 | Causey et al. ............... 600/300 |
| 6,071,294 A | 6/2000 | Simons et al. | 6,790,178 B1 | 9/2004 | Mault et al. |
| 6,071,391 A | 6/2000 | Gotoh et al. | 6,968,294 B2 | 11/2005 | Gutta et al. |

| | | | | | | |
|---|---|---|---|---|---|---|
| 7,041,468 B2 | 5/2006 | Drucker et al. | | JP | 2000-000231 | 1/2000 |
| 2001/0016310 A1 | 8/2001 | Brown et al. | | JP | 2000-116628 | 4/2000 |
| 2001/0032278 A1 | 10/2001 | Brown et al. | | WO | WO 86/00513 | 1/1986 |
| 2001/0047125 A1 | 11/2001 | Quy | | WO | WO 87/06040 | 10/1987 |
| 2001/0049096 A1 | 12/2001 | Brown | | WO | WO 89/02246 | 3/1989 |
| 2002/0016530 A1 | 2/2002 | Brown | | WO | WO 90/00367 | 1/1990 |
| 2002/0019748 A1 | 2/2002 | Brown | | WO | WO 95/06240 | 3/1995 |
| 2002/0063060 A1 | 5/2002 | Gascoyne et al. | | WO | WO 96/07908 | 3/1996 |
| 2002/0081559 A1 | 6/2002 | Brown et al. | | WO | WO 97/20207 | 6/1997 |
| 2002/0083461 A1 | 6/2002 | Hutcheson et al. | | WO | WO 97/41421 | 11/1997 |
| 2003/0050537 A1 | 3/2003 | Wessel | | WO | WO 97/46868 | 12/1997 |
| 2003/0072424 A1* | 4/2003 | Evans et al. ............ 379/106.02 | | WO | WO 98/09167 | 3/1998 |
| 2003/0083114 A1* | 5/2003 | Lavin et al. .............. 455/569.2 | | WO | WO 98/24366 | 6/1998 |
| 2003/0176183 A1 | 9/2003 | Drucker et al. | | WO | WO 98/52045 | 11/1998 |
| 2004/0030226 A1* | 2/2004 | Quy ........................... 600/300 | | WO | WO 99/05966 | 2/1999 |
| 2004/0138588 A1 | 7/2004 | Saikley | | WO | WO 99/32883 | 7/1999 |
| 2005/0019848 A1* | 1/2005 | Lee et al. ....................... 435/14 | | WO | WO 00/13580 | 3/2000 |
| 2005/0203349 A1* | 9/2005 | Nanikashvili ............... 600/300 | | WO | WO 00/20626 | 4/2000 |
| 2005/0239156 A1 | 10/2005 | Drucker et al. | | WO | WO 00/33065 | 6/2000 |
| 2005/0277164 A1 | 12/2005 | Drucker et al. | | WO | WO 00/78210 | 12/2000 |
| | | | | WO | WO 01/24038 | 4/2001 |
| FOREIGN PATENT DOCUMENTS | | | | WO | WO 01/33216 | 5/2001 |
| EP | 1 579 690 | 11/1980 | | WO | WO 01/52727 | 7/2001 |
| EP | 0 504 835 A2 | 9/1992 | | WO | WO 01/57238 | 8/2001 |
| EP | 0 653 718 A3 | 5/1995 | | WO | WO 01/57239 | 8/2001 |
| EP | 0 800 082 A2 | 10/1997 | | WO | WO 01/67009 | 9/2001 |
| EP | 0 880 936 A2 | 12/1998 | | WO | WO 02/078512 A2 | 10/2002 |
| EP | 0 970 655 A1 | 1/2000 | | WO | WO 02/078512 A3 | 10/2002 |
| EP | 1394758 A1 | 3/2004 | | WO | WO03/105629 | 2/2003 |
| GB | 1 579 690 A | 11/1980 | | | | |
| GB | 2 225 637 A | 6/1990 | | * cited by examiner | | |

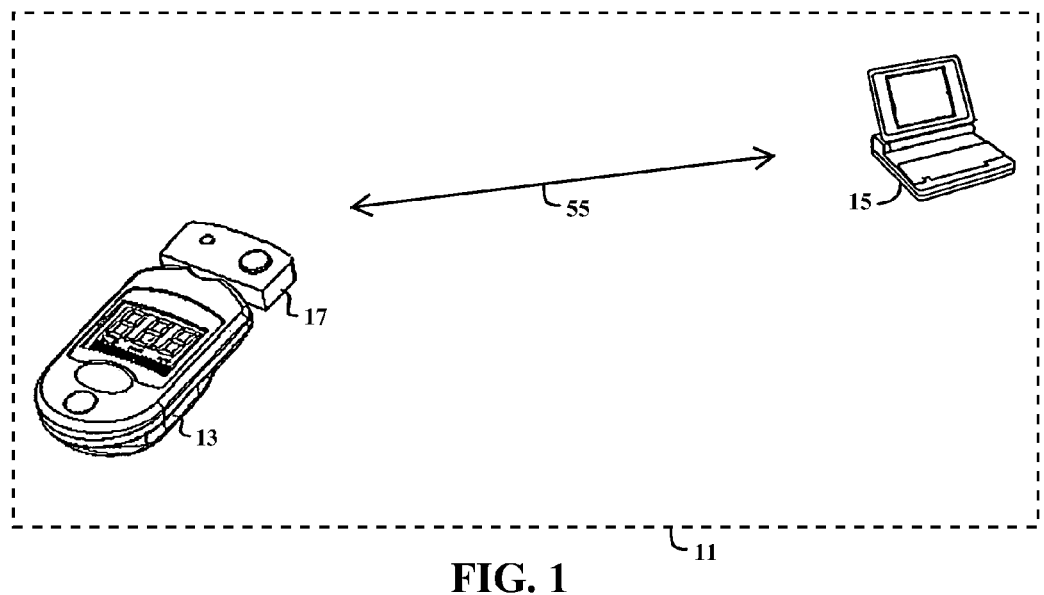
FIG. 1
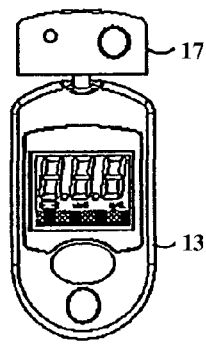 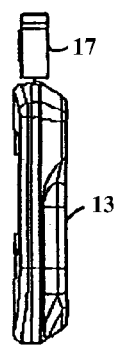 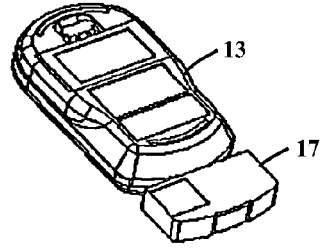
FIG. 3(a)  FIG. 3(b)  FIG. 3(c)

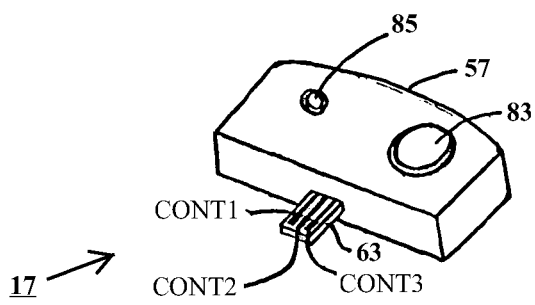
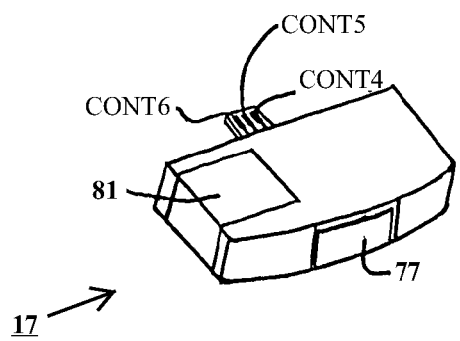
FIG. 6(a)
FIG. 6(b)
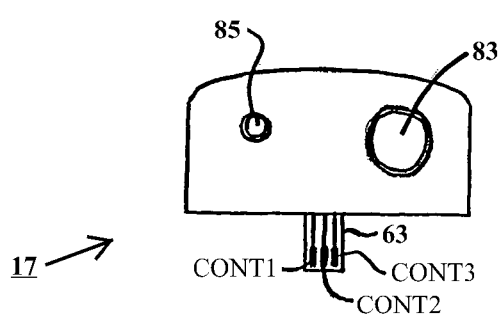
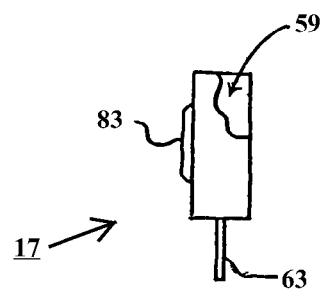
FIG. 6(c)
FIG. 6(d)

METHOD AND SYSTEM FOR TRANSFERRING ANALYTE TEST DATA

BACKGROUND OF THE INVENTION

The present invention relates generally to the field of analyte test instrument systems which can be used to perform electrochemical assays on biological samples. More particularly, the present invention relates to analyte test instrument systems which include an adaptor for transferring data stored on an analyte test instrument (e.g., a blood glucose monitor) to a data management device (e.g., a computer).

For many patients, the concentration of a particular analyte in blood must be routinely measured. The results of an analyte concentration measurement may, in turn, necessitate the patient to undertake a particular course of action in response thereto (e.g., requiring the patient to partake in a particular drug treatment).

Diabetes is a disease which typically requires a patient to routinely monitor the concentration of glucose in his/her blood. In particular, a patient suffering from diabetes is often required to measure the concentration of glucose in his/her blood multiple times each day. Based upon the results of each blood glucose measurement, the patient may require a particular drug treatment (e.g., an injection of insulin) in order to regulate that the blood glucose level of the patient remains within a specified range. Exceeding the upper limit of said range (hyperglycemia) or dropping beneath the lower limit of said range (hypoglycemia) should be avoided with as much diligence as possible to prevent the patient from experiencing serious medical complications which include, inter alia, retinopathy, nephropathy, and neuropathy.

Analyte test instrument systems are well known and are widely used in the art to perform routine electrochemical assays on biological samples. A blood glucose monitoring system is one well-known type of analyte test instrument system which is used to perform routine glucose concentration tests on blood samples.

One type of blood glucose monitoring system which is well known and widely used in the art comprises at least one disposable test strip which electrochemically reacts in response to the deposition of a blood sample thereon. The test strip is designed for use with a corresponding blood glucose monitor which calculates the concentration of blood glucose in the blood sample based upon the electrochemical reaction between the test strip and the blood sample. Examples of blood glucose monitoring systems of the type described above are manufactured and sold by Abbott Laboratories, Medisense Products of Bedford, Mass. under the PRECISION line of blood glucose monitoring systems.

A disposable, blood glucose monitoring test strip typically comprises a thin base, or substrate, layer which is generally rectangular in shape. A plurality of electrical contacts, or strips, are deposited along substantially the entire length of the base layer in a spaced apart, parallel relationship. One end of the electrical contacts is positioned within the reaction area of the test strip. In the reaction area of the test strip, an enzyme is deposited which is capable of reacting with the glucose in a blood sample to produce a measurable electrical response. The other end of the electrical contacts is disposed to electrically contact associated conductors located in the blood glucose monitor, as will be described further below.

A blood glucose monitor is typically modular and portable in construction to facilitate its frequent handling by the patient. A blood glucose monitor often comprises a multi-function test port which is adapted to receive the test strip in such a manner so that an electrical communication path is established therebetween. As such, an electrical reaction created by depositing a blood sample onto the reaction area of the test strip travels along at least one of the conductors of the test strip and into the test port of the blood glucose monitor. Within the housing of the monitor, the test port is electrically connected to a microprocessor which controls the basic operations of the monitor. The microprocessor, in turn, is electrically connected to a memory device which is capable of storing a multiplicity of blood glucose test results.

In use, a blood glucose monitor of the type described above can be used in the following manner to measure the glucose level of a blood sample and, in turn, store the result of said measurement into memory as test data. Specifically, a disposable test strip is inserted into the test port of the monitor. With the test strip properly inserted into the monitor, there is established a direct electrical contact between the conductors on the test strip and the conductors contained within the test port, thereby establishing an electrical communication path between the test strip and the monitor through which electrical signals can travel. Having properly disposed the test strip into the test port, the monitor typically displays a "ready" indication on its display.

The user is then required to deposit a blood sample onto the reaction area of the test strip, the acquisition of the blood sample typically being accomplished by pricking the fingertip of the patient with a lancing device. When a sufficient quantity of blood is deposited on the reaction area of the test strip, an electrochemical reaction occurs between the blood sample and the enzyme present in the reaction area which, in turn, produces an electrical current which decays exponentially over time.

The decaying electrical current created through the chemical reaction between the enzyme and the glucose molecules in the blood sample, in turn, travels along the electrically conductive path established between the test strip and the monitor and is measured by the microprocessor of the monitor. The microprocessor of the monitor, in turn, correlates the declining current to a standard numerical glucose value. The numerical glucose value calculated by the monitor is then shown on the monitor display for the patient to observe. In addition, the data associated with the particular blood glucose measurement is stored into the memory for the monitor.

It should be noted that blood glucose monitors of the type described above often include a memory device which is capable of storing a number of different events, wherein examples of some possible events include, but are not limited to, a blood glucose measurement, a calibration function, and a date/time change for the monitor. In fact, some blood glucose monitors are capable of storing in memory as many as 400 events at a single time.

In order to effectively monitor the blood glucose level patterns of a patient, a clinician and/or physician for a diabetes patient often downloads a series of blood glucose monitoring events onto a data management device, such as a computer, which is loaded with comprehensive data management system (DMS) software (e.g., the PRECISION LINK data management system software which is manufactured and sold by Abbott Laboratories, MediSense Products of Bedford, Mass.) capable of retrieving, managing and analyzing the data stored on the monitor. In particular, a clinical analyst and/or a physician for a diabetes patient is often interested in tracking the blood glucose levels of a patient over a fixed period of time (e.g., 1 month).

In order to effectively track the blood glucose levels of a patient over a fixed time, a clinical analyst and/or a physician is required to periodically meet with the patient and download all of the data stored in the blood glucose monitor into the data management device for comprehensive analysis. Analyzing the test results in this manner, the clinician and/or physician is able to assess how effectively the patient is able to regulate his/her blood glucose level.

Traditionally, the data stored on a blood glucose monitor is downloaded onto a data management device using a hardwire communication link. A hardwire communication link typically comprises a communication cable which, at one end, is provided with a test strip-shaped communication interface which can be removably inserted into the strip port of the blood glucose monitor and, at the other end, is provided with a connector which is adapted to removably connect with the serial port of a conventional computer.

As can be appreciated, a diabetes patient is somewhat limited in the frequency in which he/she can visit a clinician and/or physician to track glucose test results. As a result, diabetes patients are encouraged to frequently download the data stored on the blood glucose monitor onto his/her own computer for comprehensive analysis. In this manner, a diabetes patient can monitor his/her test results as frequently as desired (e.g., daily, weekly, etc.).

However, the process of electrically connecting a blood glucose monitor to a computer using a hardwire communication link has been found by some diabetes patients to be cumbersome, complicated, and time consuming. Overwhelmed by the connection process, some patients download their blood glucose levels onto a computer for further analysis less frequently than is desired, thereby increasing the patient's risk of experiencing a serious diabetes related medical complication, which is highly undesirable.

SUMMARY OF THE INVENTION

It is an object of the present invention to provide a method and system for wirelessly transferring analyte test data stored on an analyte test instrument, such as a blood glucose monitor, to a data management device, such as a computer.

It is another object of the present invention to provide a method and system for transferring analyte test data stored on an analyte test instrument to a data management device via an adaptor.

It is yet another object of the present invention to provide a method and system as described above wherein the adaptor can be removably connected to the analyte test instrument.

It is yet still another object of the present invention to provide a method and system as described above which has a limited number of parts, which is inexpensive to manufacture and which is easy to use.

Therefore, according to one feature of the present invention, there is provided a system for transferring data comprising an analyte test instrument which is adapted to store data, an adaptor removably connected to said analyte test instrument, said adaptor being in data communication with said analyte test instrument through a first data communication channel, and a data management device in data communication with said adaptor through a second data communication channel, said second communication channel being a wireless data communication channel.

According to another feature of the present invention, there is provided an adaptor for transferring data stored on an analyte test instrument to a wirelessly enabled data management device, said analyte test instrument comprising a data communication device, said adaptor comprising a data communication device, said data communication device for said adaptor being adapted to removably connect with the data communication device of said analyte test instrument so as to establish a first data communication channel between said adaptor and said analyte test instrument, a microcontroller in electrical connection with said data communication device for said adaptor, a wireless controller in electrical connection with said microcontroller, and a wireless transceiver in electrical connection with said wireless controller, said wireless transceiver being adapted to wirelessly communicate with said data management device through a second data communication channel.

According to another feature of the present invention, there is provided a method for transferring data stored on an analyte test instrument to a data management device via an adaptor, said adaptor being independent from said analyte test instrument, said method comprising the steps of removably connecting said adaptor to said analyte test instrument so as to establish a first data communication channel between said adaptor and said analyte test instrument, transferring data stored on said analyte test instrument to said adaptor through the first data communication channel, and transmitting the transferred data from said adaptor to said data management device through a second data communication channel, the second data communication channel being a wireless data communication channel.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts:

FIG. 1 is a perspective view of a first embodiment of a system for transferring analyte test data, said system being constructed according to the teachings of the present invention, the adaptor being shown connected to the analyte test instrument, the adaptor being shown in wireless communication with the data management device;

FIG. 3(a) is a front plan view of the analyte test instrument and the adaptor shown in FIG. 1, the adaptor being shown connected to the analyte test instrument;

FIG. 3(b) is a right side view of the analyte test instrument and the adaptor shown in FIG. 1, the adaptor being shown connected to the analyte test instrument;

FIG. 3(c) is a rear perspective view of the analyte test instrument and the adaptor shown in FIG. 1, the adaptor being shown connected to the analyte test instrument;

FIG. 6(a) is an enlarged, front perspective view of the adaptor shown in FIG. 1;

FIG. 6(b) is an enlarged, rear perspective view of the adaptor shown in FIG. 1;

FIG. 6(c) is an enlarged, front plan view of the adaptor shown in FIG. 1;

FIG. 6(d) is an enlarged, right side view, broken away in part, of the adaptor shown in FIG. 1;

DETAILED DESCRIPTION OF THE PREFERRED EMBODIMENT

Figure 2:
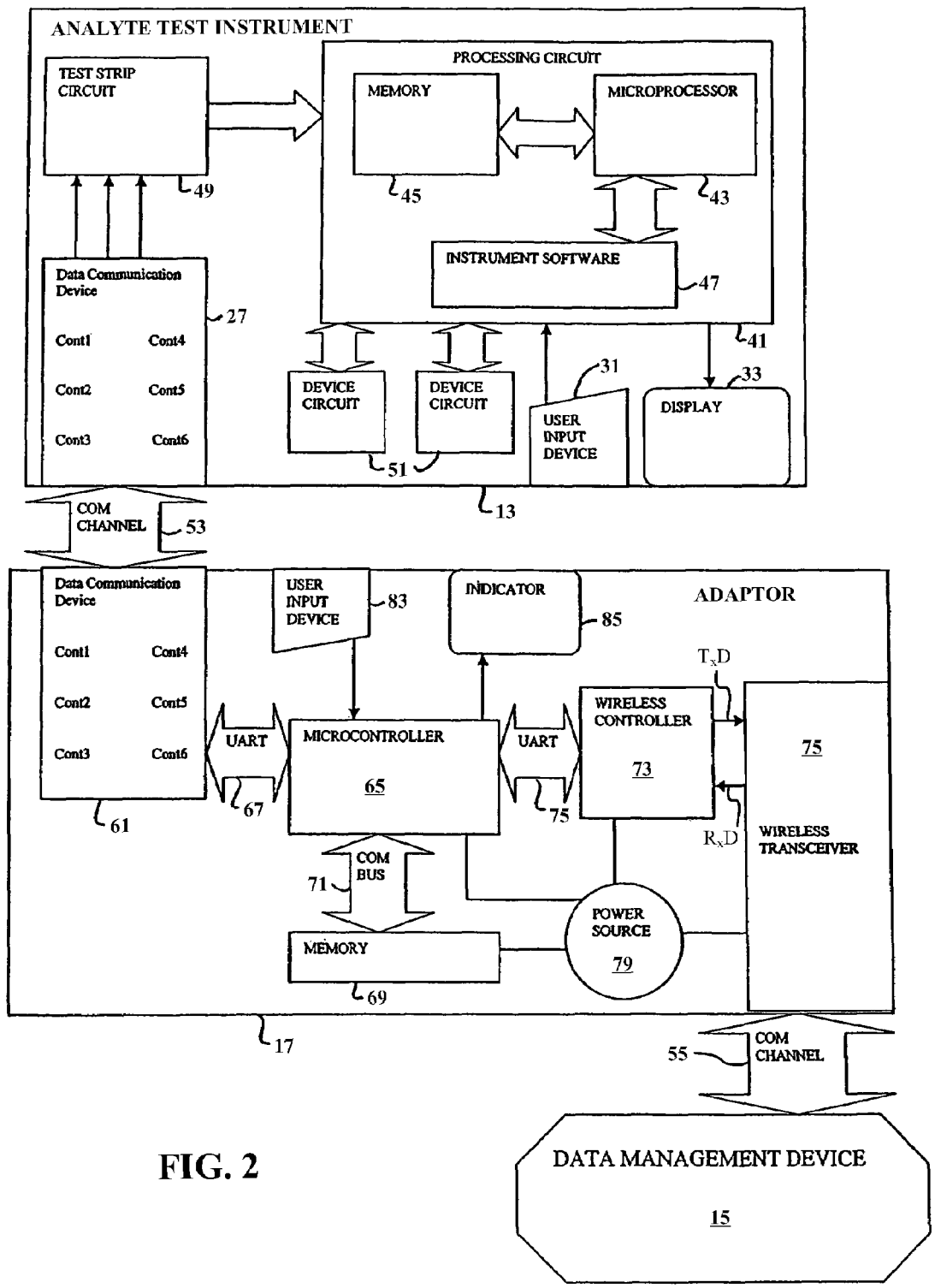
FIG. 2 is a simplified block diagram of the system shown in FIG. 1.

Referring now to FIGS. 1 and 2, there is shown a first embodiment of a system for transferring data, said system being constructed according to the teachings of the present invention and identified generally by reference numeral 11.

System 11 comprises an analyte test instrument (ATI) 13, a data management device (DMD) 15, and an adaptor 17. As will be described further in detail below, analyte test data stored in ATI 13 can be wirelessly transmitted to DMD 15 via adaptor 17.

Analyte test instrument 13 represents a monitor which can be used to measure the concentration of an analyte in a test sample. As is shown herein, ATI 13 is in the form of a conventional blood glucose monitor (e.g., an electrochemical or photometric blood glucose monitor). As such, ATI 13 is capable of measuring glucose concentrations of a blood sample and, in turn, storing the results of each blood glucose measurement as data in memory. As an example, ATI 13 may be of the type disclosed in U.S. Pat. No. 6,377,894 to Deweese et al, which is incorporated herein by reference.

ATI 13 is a communication enabled device. In this respect, ATI 13 is capable of serial data transfer with another device (e.g., adaptor 17), as will be described further in detail below.

Figure 4:
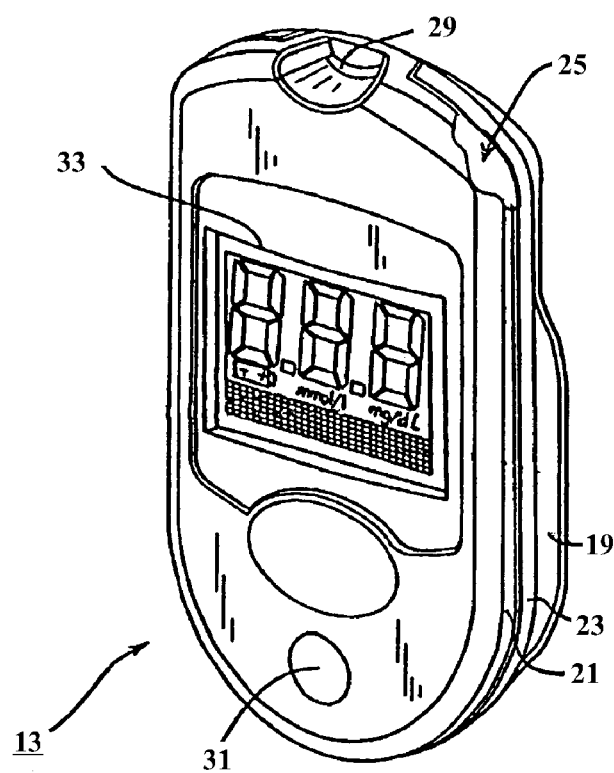
FIG. 4 is an enlarged front perspective view, broken away in part, of the analyte test instrument shown in FIG. 1.

Referring now to FIGS. 2-4, ATI 13 is a modular, self-contained, and portable unit which comprises a protective housing 19 constructed of a durable and inexpensive material, such as plastic. Housing 19 includes a front casing 21 and a rear casing 23 which are secured together by means of a snap-fit interconnection. With front casing 21 and rear casing 23 affixed together, housing 19 is a substantially enclosed device which is shaped to include an interior cavity 25 into which the electrical and electronic components of ATI 13 are disposed, as will be described further below.

ATI 13 comprises a data communication device 27 which is disposed within interior cavity 25 of housing 19 and which is accessible through a slot 29 formed into the top of housing 19. Data communication device 27 is a current source sensing device which is capable of transmitting and receiving serial data. In the present embodiment, data communication device 27 is in the form of a conventional multi-purpose test port which includes a slot shaped to matingly receive and electrically connect with, inter alia, a test strip, a calibration strip, or the interface connector of a hardwire communication link. Data communication device 27 comprises six metal contact strips, which are identified as contact strips Cont1 through Cont6 in FIG. 2.

It should be noted that data communication device 27 is not limited to a conventional multi-purpose test port. Rather, it is to be understood that data communication device 27 could be in the form of any conventional communication device which is capable of transmitting and receiving serial data without departing from the spirit of the present invention. As one example, data communication device 27 could alternatively be in the form of a wireless transceiver without departing from the spirit of the present invention. As another example, data communication device 27 could alternatively be in the form of a phone jack receptacle without departing from the spirit of the present invention, which will be described further in detail below.

ATI 13 also comprises a user input device 31 which is disposed within interior cavity 25 and which at least partially projects through an opening formed in front casing 21 of housing 19. User input device 31 is shown herein as being in the form of a button capable of being manually depressed. In use, input device 31 is for the manual regulation of a switch which, in turn, controls operative functions for ATI 13. In particular, input device 31 enables the user to regulate the power state of ATI 13, to recall information stored in memory, to respond to messages provided in the display, to provide access to menus generated by software contained within ATI 13, and to set some of the configuration control parameters.

Figure 5:
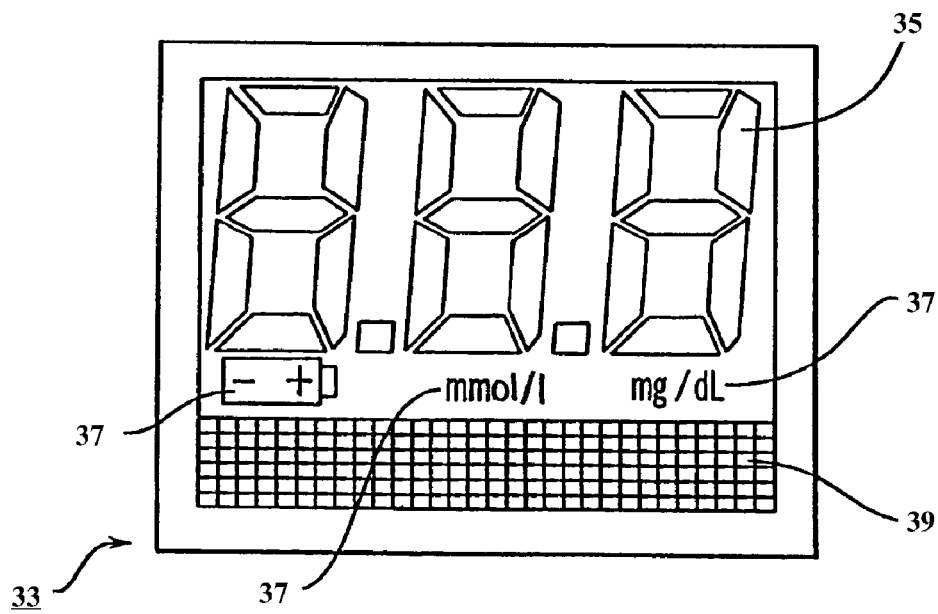
FIG. 5 is an enlarged front plan view of the display for the analyte test instrument shown in FIG. 1.

ATI 13 further comprises a display 33 which is disposed within interior cavity 25 and which is viewable through a transparent window formed in front casing 21 of housing 19. Display 33 is shown herein as being in the form of a screen designed to provide the user with information in a visual form. As can be seen most clearly in FIG. 5, display 33 is in the form of a liquid crystal display (LCD) which is used to display, inter alia, test results, user messages, and recalled information which is stored in the memory of ATI 13. Display 33 includes a numerical display 35 which is capable of generating three, seven-segment digital numbers. As can be appreciated, display 35 provides the user with a means for visually indicating the numerical value associated with a particular test result, display 35 including a pair of decimal point indicators to allow for a wider range of possible output values. Display 33 also comprises a plurality of icons 37 which indicate the units of measurement of a test result (e.g., mg/dL or mmol/l) and a low battery condition. Display 33 further comprises a dot-matrix message line 39 which can be used to provide information to the user, message line 39 being capable of generating up to 10 numerals or up to 9 characters at the same time. The information displayed by message line 39 can include, among other things, time and data information, user prompts (e.g., "apply blood"), error messages (e.g., "expired strip"), and configuration control settings (e.g., setting time or selecting a operating language).

It should be noted that the information shown on display 33 is controlled by display driver software for ATI 13. The display driver software provides display 33 with the ability to scroll a long message, flash a message or a portion of a message, or display alternating messages. In addition, the display driver software can provide ATI 13 with the ability to flash icons 37. Furthermore, as ATI 13 is powering up, the display driver software can support a visual check of display 33 wherein the icons and pixels for display 33 are turned on for a brief period to enable the user to confirm the entire display 33 is functioning properly.

ATI 13 preferably derives power from a power source (not shown) disposed within interior cavity 25. The power source may be in the form of one or more replaceable AA-type batteries which are removably mounted into an associated battery compartment in interior cavity 25 and which are accessible through a removable cover formed into rear casing 23 of housing 19. However, it is to be understood that any source of power capable of providing a suitable direct (DC) voltage can be used to provide power to ATI 13.

As seen most clearly in FIG. 2, user input 31 and display 33 are connected to a processing circuit 41 which, in turn, is connected to a microprocessor 43, memory 45, and instrument software 47. In addition, data communication device 27 is connected to processing circuit 41 through a test strip circuit 49.

Processing circuit 41 is an application specific integrated circuit (ASIC) which enables a test strip is inserted into direct electrical connection with data communication device 27 to communicate with microprocessor 43. For example, processing circuit 41 enables microprocessor 43 to send signals to data communication device 27 to determine the identity of a strip which is disposed into electrical connection therewith (i.e., to determine whether the strip is a calibration strip, a test strip, or the strip-like interface connector for a communication link). Microprocessor 43 may determine the identity of a strip disposed into electrical connection with data communication device 27 by measuring the impedance of said strip or by detecting the location of the electrical contacts on said strip.

Microprocessor 43 is an application specific integrated circuit (ASIC) that functions as the central processing unit for ATI 13. As such, microprocessor 43 performs the principal calculation and data management tasks for ATI 13.

Memory 45 is connected to microprocessor 43 and serves to retain data processed by microprocessor 43, said data being available for subsequent retrieval. Types of information that may be stored in memory 45 include measurement delay times, sample incubation times, number of measurements to be taken during an assay, thresholds against which voltage levels can be compared, values of excitation voltage levels applied to a test strip during assay, analyte value conversion factors, failsafe assay threshold values, and configurations of circuitry of analyte test instrument 13. It should be noted that memory 45 has the capacity to store a multiplicity of assay results. Specifically, each assay result is typically stored into memory 45 as a data bundle referred to herein as "an event". As can be appreciated, memory 45 is preferably of the type which can store in excess of 400 events.

Instrument software 47 is provided for microprocessor 43, software 47 functioning in response to information received at data communication device 27 from a calibration strip. Specifically, instrument software 47 uses the information received from a calibration strip to control the operation of the ATI 13. Instrument software 47 also controls operations of the ATI 13 that are independent of information introduced or generated at data communications device 27. For example, instrument software 47 enables the user to recall assay results and assay information, can provide various warning, error, and prompting messages, can permit setting of date and time, can control transmission of data to external devices, can monitor power level or battery level or both, and can provide indications to the user if power drops below a specified level.

A test strip circuit 49 connects data communication device 27 to processing circuit 41. In operation, test strip circuit 49 enables data to pass between data communication device 27 and processing circuit 41.

A pair of device circuits 51 are also connected to processing circuit 41. Device circuits 51 can comprise analog, digital, or mixed-signal circuits, application-specific integrated circuits (ASICs), and passive and active electrical components. Device circuits 51 can perform various electrical functions required by ATI 13. Specifically, device circuits 51 carry instructions from microprocessor 43 to various functional components of ATI 13 so that these components can perform their intended functions. As one example, device circuits 51 may serve to drive the clock functions for microprocessor 43.

In use, ATI 13 can be used in the following manner to measure and store analyte test data. Specifically, an analyte test strip is inserted into data communication device 27 so that the metal contacts on the test strip are in direct metal-to-metal contact with the contacts CONT1 through CONT6 of data communication device 27, thereby establishing a communication channel between the test strip and ATI 13. Having inserted the test strip into data communication device 27, instrument software 47 identifies the item inserted into data communication device 27 as an analyte test strip. At this time, microprocessor 43 executes software which generates a message on display 33 that notifies the user to deposit a sample onto the test strip. When a sample is deposited onto the reaction area of the test strip, the sample reacts with enzymes in the reaction area which, in turn, produces an electrical response in the form of a decaying electrical current. Test strip circuit 49 converts the decaying current from an analog signal to a digital signal and then passes the converted signal to processing circuit 41. The converted signal is then processed by microprocessor 43 to determine the analyte test value that corresponds to the signal. Microprocessor 43 then stores the analyte test data as an event in memory 45 and simultaneously registers the analyte test value on display 33 for the patient to read.

The aforementioned analyte testing process can be repeated as desired. As noted briefly above, each test performed is preferably stored into memory 45 as an event, memory 45 being capable of storing a large quantity of events which can be subsequently retrieved and analyzed by a personal computer using sophisticated data management software.

Although ATI 13 is represented herein as being in the form of a communication enabled, blood glucose monitor, it is to be understood that ATI 13 represents any conventional communication enabled device which can be used to measure the concentration of an analyte in a sample. As an example, ATI 13 may represent any of the PRECISION line of blood glucose monitors which are manufactured and sold by Abbott Laboratories, MediSense Products of Bedford, Mass.

Data management device (DMD) 15 is represented herein as being in the form of a wirelessly enabled, laptop computer. As such, DMD 15 is capable of serial data transfer with another device (e.g., adaptor 17) through a wireless communication channel.

Preferably, DMD 15 is provided with comprehensive data analysis software (e.g., the PRECISION LINK software manufactured and sold by Abbott Laboratories, MediSense Products of Bedford, Mass.) which allows for analyte test data stored on an analyte testing device (e.g., ATI 13) to be downloaded, managed, and analyzed (e.g., charted) by DMD 15, thereby providing the patient with sophisticated analyte test data monitoring and tracking capabilities, which is highly desirable.

Although DMD 15 is represented herein as being in the form of a wirelessly enabled, laptop computer, it is to be understood that DMD 15 is not limited to a wirelessly enabled laptop computer. Rather, DMD 15 could be in the form of other types of conventional, wirelessly enabled data management devices (e.g., desktop computer, personal data assistant (PDA), printer, etc.) without departing from the spirit of the present invention.

Adaptor 17 is a modular, self-contained and portable unit which can be removably connected to ATI 13, as seen most clearly in FIGS. 3(a)-(c). As will be described further in detail below, adaptor 17 is adapted to communicate with ATI 13 by means of a first communication channel 53 and wirelessly communicate with DMD 15 by means of a second communication channel 55. In this capacity, adaptor 17 can be used to retrieve data (e.g., analyte test data) stored in memory 45 via first communication channel 53 and, in turn, wirelessly transmit said data to DMD 15 via second communication channel 55.

As seen most clearly in FIGS. 2 and 6(a)-(d), adaptor 17 comprises a protective housing 57 constructed of a durable and inexpensive material, such as plastic. Housing 57 is a substantially enclosed device which is shaped to define an interior cavity 59 which is shaped to substantially receive the electrical and electronic components of adaptor 17, as will be described further below.

Adaptor 17 comprises a data communication device 61 disposed within interior cavity 59 and which partially and fittingly protrudes out through a narrow slot formed in the bottom of housing 57. Data communication device 61 is a communication device which is capable of electrically connecting with data connection device 27 of ATI 13, so as to establish communication channel 53 between ATI 13 and adaptor 17 through which data can be transmitted and received.

In the present embodiment, the portion of data communication device 61 which extends out from housing 57 is in is in the form of a rectangular strip 63 having the same approximate width and thickness as a test strip used in conjunction with data communication device 27. Six metal contact strips, which are identified as contact strips Cont1 through Cont6 in FIGS. 2 and 6(a)-(c), are deposited along substantially the entire length of strip 63 in a spaced apart, parallel relationship. As such, when strip 63 of data communication device 61 is inserted into the test port configuration of data communication device 27, each of the contact strips, or leads, on data communication device 61 is disposed in direct conductive contact with an associated contact strip within the test port. In this manner, with data communication device 61 properly inserted into the test port slot for data communication device 27, communication channel 53 is established between ATI 13 and adaptor 17 through which serial data is capable of being transferred.

It should be noted that the particular construction of data communication device 61 enables adaptor 17 to be removably connected to ATI 13. As a result, adaptor 17 can be manufactured and stored separately from ATI 13, adaptor 17 being connected to ATI 13 to form communication channel 53 only when the user desires to send data from ATI 13 to DMD 15.

As can be appreciated, the ability to removably connect adaptor 17 to ATI 13 provides the user with a number of significant advantages. As a first advantage, when the user only desires to store data onto ATI 13 and is not interested in wirelessly transmitting said data to DMD 15, adaptor 17 can be separated from ATI 13, thereby reducing the overall size and weight of the unit, which is highly desirable. As a second advantage, the particular construction of data communication device 61 enables adaptor 17 to be used in conjunction with many types of pre-existing types of analyte test instruments. As a result, a patient who owns a pre-existing ATI which is compatible with adaptor 17 can wirelessly transmit data stored on said pre-existing ATI to a data management device, such as a computer, simply by purchasing adaptor 17, which is highly desirable.

It should be noted that data communication device 61 is not limited to the test strip-type configuration shown herein. Rather, it is to be understood that data communication device 61 could be in the form of alternative types of conventional communication devices which are capable of transmitting and receiving serial data without departing from the spirit of the present invention. Specifically, data communication device 27 and data communication device 61 represent any compatible means for establishing a communication channel (e.g., wireless, hardwire) therebetween. As will be described further in detail below, data communication device 61 may be in the form of a male, phone jack and data communication device 27 may be in the form of a female, phone jack receptacle without departing from the spirit of the present invention.

Data communication device 61 is electrically connected to a microcontroller 65 via universal asynchronous receiver transmitter (UART) communication bus 67, microcontroller 65 being disposed within interior cavity 59 of housing 57. Microcontroller 65 is an application specific integrated circuit (ASIC) which functions as the central processing unit for adaptor 17. As such, microcontroller 65 is responsible for, inter alia, the processing and managing of data which is retrieved from ATI 13 and wirelessly transmitted to DMD 15, as will be described further in detail below.

For purposes of the present specification and claims, the term microcontroller shall mean microcontroller or microprocessor unless otherwise specified.

Memory 69 is disposed within interior cavity 59 of housing 57 and is electrically connected to microcontroller 65 through a communication bus 71. As will be described further below, memory 69 serves two principal functions. As a first function, memory 69 stores the application code software for adaptor 17. As a second function, memory 69 temporarily stores (i.e., buffers) the data retrieved from ATI 13 prior to its transmission to DMD 15. It should be noted that memory 69 preferably includes two separate memory devices, one of said memory devices being responsible for storing the application code software for adaptor 17 and the other of said memory device being responsible for temporarily storing the data retrieved from ATI 13 prior to its transmission to DMD 15.

A wireless controller 73 is disposed within interior cavity 59 of housing 57 and is electrically connected to microcontroller 65 via universal asynchronous receiver transmitter (UART) communication bus 75. As will be described further in detail below, in response to commands sent by microncontroller 65, wireless controller 73 serves to regulate the operation of a wireless transceiver 75.

For purposes of the present specification and claims, wireless controller 73 represents both a component which is physically separate from microcontroller 65 as well as a component which is physically incorporated into microcontroller 65 to form an integrated device unless otherwise specified.

Wireless transceiver 75 is disposed within interior cavity 59 of housing 57 and is electrically is connected to wireless controller 73 via a transmitter line TxD and a receiver line RxD, electrical signals passing from controller 73 to transceiver 75 traveling via transmitter line TxD and electrical signals passing from transceiver 75 to controller 73 traveling via receiver line RxD. As will be described further in detail below, wireless transceiver 75 serves to transmit electrical signals to DMD 15 and receive electrical signals from DMD 15. Preferably, wireless transceiver 75 is disposed within interior cavity 59 in close proximity to a window 77 formed into the top of housing 17 through which signals are capable of traveling.

It should be noted that wireless transceiver 75 represents any conventional transceiver which is capable of two-way communication with a communication enabled device. As a result, wireless communication channel 55 represents any conventional two-way wireless communication channel (e.g., infrared (IR), such as infrared data (IrDA), or radio frequency (RF), such as Bluetooth, 802.11, Zigbee).

A power source 79 is disposed within interior cavity 59 of housing 57 and is electrically connected to microcontroller 65, memory 69, wireless controller 73 and wireless transceiver 75. Power source 79 is preferably in the form of a replaceable 3 volt, coin cell lithium battery which is accessible through a door 81 which is slidably mounted onto housing 57. However, it is to be understood that power source 79 is not limited to a 3 volt, coin cell lithium battery. Rather, it is to be understood that power source 79 could be in the form of additional types of conventional power sources (e.g., a solar battery cell) without departing from the spirit of the present invention. In addition, it is to be understood that power source 79 could be eliminated entirely from adaptor 17 without departing from the spirit of the present invention. Specifically, if power source 79 were to be removed from adaptor 17, power could alternatively be supplied to adaptor 17 from the power source of ATI 13.

A user input device 83 is disposed within interior cavity 59 and is sized and shaped to fittingly project through a corresponding opening formed in the front of housing 57. User input device 83 is preferably in the form of a circular button which can be manually depressed so as to selectively close a switch which is electrically connected to microcontroller 65. As will be described further below, input device 83 serves as a finger actuable means for triggering the execution of the data transfer from adaptor 17 to DMD 15.

An indicator 85 is disposed within interior cavity 59 and is sized and shaped to fittingly project through a corresponding opening formed in the front of housing 57. Indicator 85 is preferably in is in the form of a green light emitting diode (LED) which is electrically connected to microcontroller 65. As will be described further in detail below, indicator 85 serves as a means for providing the user with a visual indication of the operating state of indicator (e.g., whether indicator 85 is transferring data to DMD 15).

As noted above, system 11 is capable of transferring data stored in memory 45 of ATI 13 to DMD 15 via adaptor 17. As will be described further below, system 11 transfers data stored on ATI 13 to DMD 15 via adaptor 17 by means of a two-step process. In the first step of the two step process, data stored in memory 45 of ATI 13 is transferred into buffer memory 69 of adaptor 17. In the second step of the two step process, data transferred into buffer memory 69 of adaptor 17 is, in turn, wirelessly transmitted to DMD 15. Each of the two aforementioned steps will be discussed further in detail below.

Figure 7:
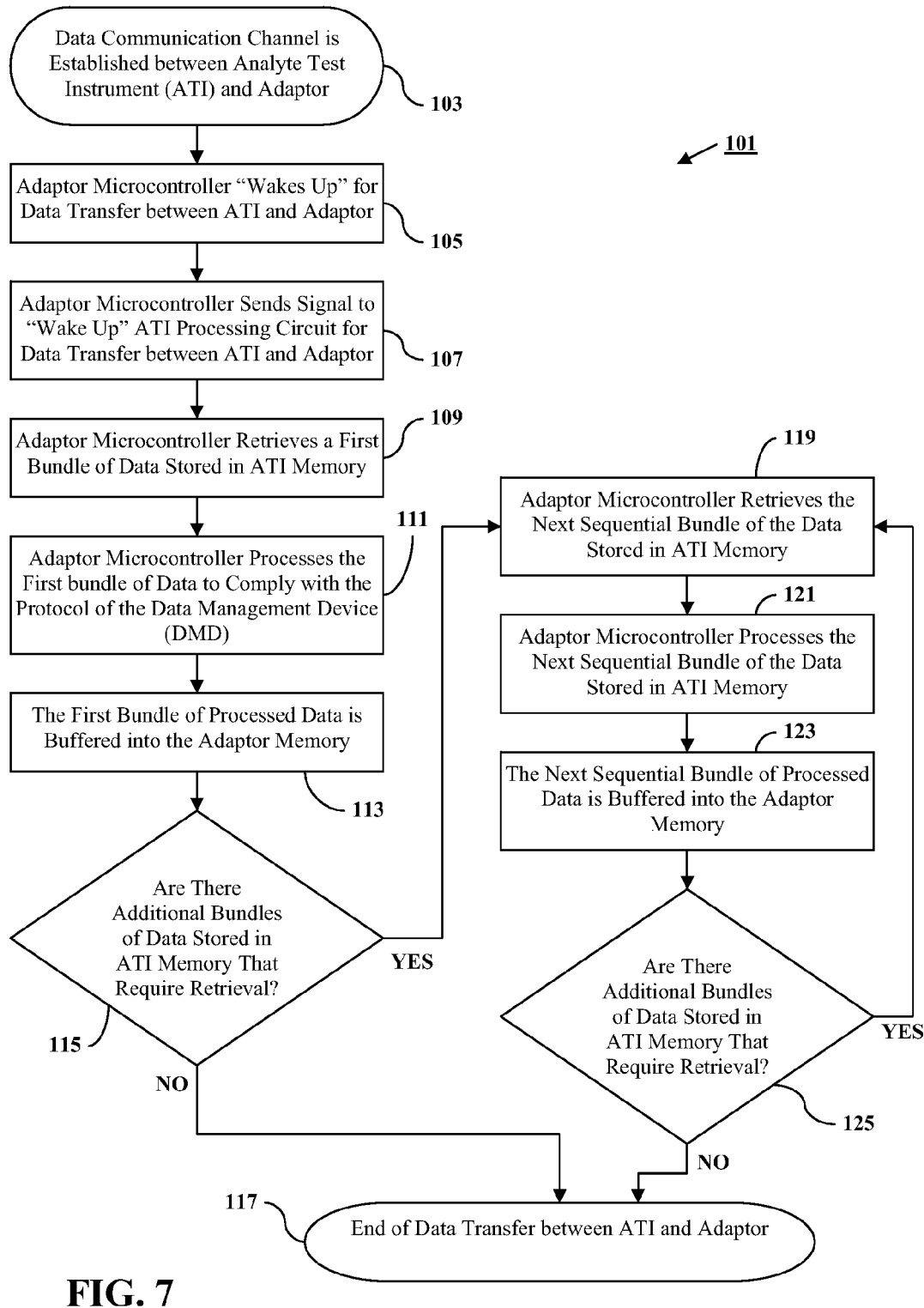
FIG. 7 is a flow chart depicting the method in which the system shown in FIG. 1 transfers data from the analyte test instrument to the adaptor.

FIG. 7 is a flow chart illustrating the method in which system 11 transfers data from ATI 13 to adaptor 17, said method being represented generally by reference numeral 101. Method 101 commences once data communication channel 53 is established between ATI 13 and adaptor 17, said step being represented by reference numeral 103. It should be noted that, for system 11, data communication channel 53 is established between ATI 13 and adaptor 17 by inserting strip 63 of data communication device 61 into the corresponding test port slot of data communication device 27, wherein the electrical conductors on data communication device 61 are disposed in direct electrical contact against the electrical conductors within data communication device 27.

Having established data communication channel 53 between ATI 13 and adaptor 17 in step 103, adaptor microcontroller 65 becomes active, or "wakes up", in anticipation of the transfer of data between ATI and adaptor 17, said step being represented by reference numeral 105. Specifically, once data communication channel 53 has been established between ATI 13 and adaptor 17, the protocol for ATI 13 is to send out a signal to determine the type of device (e.g., adaptor, analyte test strip, calibration test strip) connected to data communication device 27. It is this signal sent by ATI 13 to determine the type of device connected to data communication device 27 which, in turn, serves to activate adaptor microcontroller 65. Once adaptor microcontroller 65 becomes active, adaptor microcontroller 65 then sends a signal to activate, or "wake up", microprocessor 43 for ATI 13 in anticipation of data transfer between ATI 13 and adaptor 17, said step being represented by reference numeral 107.

With adaptor microcontroller 65 and ATI microprocessor 43 having been activated in steps 105 and 107, adaptor microcontroller 65 receives a first bundle of data stored in memory 45 of ATI 13, said step being represented by reference numeral 109. It should be noted that adaptor microcontroller 65 is programmed to understand the protocol of ATI 13 (e.g., ASTM 1381 protocol) and, as a result, can recognize the particular bundles, or packets, of data stored in memory 45 of ATI 13. Having received the first bundle of data in step 109, adaptor microcontroller 65 processes (i.e., reformats and sorts) the first bundle of data in order to render said bundle in compliance with the data receiving protocol for DMD 15, said step being represented by reference numeral 111. In step 113, the first bundle of processed data in microcontroller 65 is then buffered into memory 69.

Having completed the transfer of the first bundle of data from memory 45 of ATI 13 to buffer memory 69 of adaptor 17, microcontroller 65 then sends a signal to microprocessor 43 to determine whether additional bundles of data remain in memory 45 for ATI 13 that need to be retrieved by adaptor 17, said step being represented by reference numeral 115. If there are no additional bundles of data located in memory 45 of ATI 13, the data transfer process between ATI 13 and adaptor 17 ends, as represented by reference numeral 117.

However, if additional bundles of data are located in memory 45 of ATI 13, adaptor microcontroller 65 receives the next sequential bundle of data stored in memory 45 of ATI 13, said step being represented by reference numeral 119. Having received the next sequential bundle of data in step 119, adaptor microcontroller 65 processes said bundle of data in step 121. In step 123, said bundle of processed data in microcontroller 65 is then buffered into memory 69.

Having completed the transfer of the next sequential bundle of data from ATI 13 to adaptor 17, microcontroller 65 then sends an additional signal to microprocessor 43 to determine whether more bundles of data remain in memory 45 of ATI 13 that need to be retrieved by adaptor 17, said step being represented by reference numeral 125. If there are no additional bundles of data located in memory 45, method 101 proceeds to step 117. However, if additional bundles of data are located in memory 45 of ATI 13, method 101 returns to step 119. As such, method 101 continues until all the bundles of data in memory 45 for ATI 13 are properly transferred into memory 69 for adaptor 17.

Figure 8:
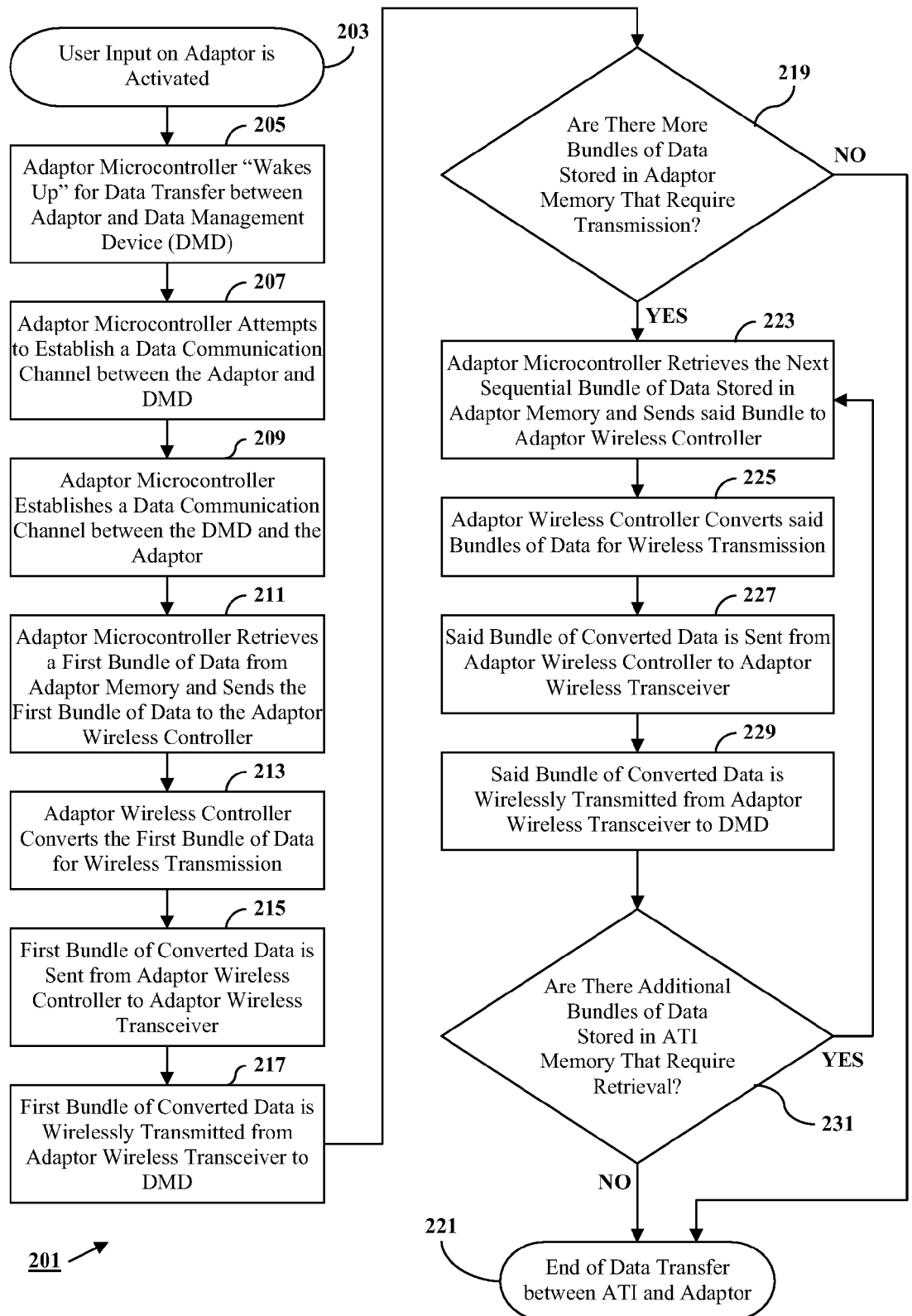
FIG. 8 is a flow chart depicting the method in which the system shown in FIG. 1 wirelessly transmits data from the adaptor to the data management device.

Having completed the first step of the two-step process for transferring data from ATI to DMD 15 via adaptor 17, system 11 is now prepared to execute the second step of the two-step process for transferring data from ATI 13 to DMD 15 via adaptor 17. More specifically, system 11 is now prepared to wirelessly transmit the data buffered into memory 69 of adaptor 17 to wirelessly enabled DMD 15. FIG. 8 is a flow chart illustrating the method by which system 11 transfers data from memory 69 of adaptor 17 to DMD 15, said method being represented generally by reference numeral 201.

Method 201 commences once user input device 83 on adaptor 17 is activated (i.e., depressed), said step being represented by reference numeral 203. The activation of user input device 83 in step 203, causes adaptor microcontroller 65 to become active, or "wake up", in anticipation of data transfer between adaptor 17 and DMD 15, said step being represented by reference numeral 205.

Once activated, adaptor microcontroller 65 instructs wireless controller 73 to have wireless transceiver 75 send out a signal through window 77 in order to establish a data communication channel 55 between adaptor 17 and DMD 15, said step being represented by reference numeral 207. It should be noted that during step 207, adaptor microcontroller 65 simultaneously instructs indicator 85 to provide a signal (e.g., a flashing green light) to notify the user of the attempt by adaptor 17 to establish a data communication channel 55 with DMD 15. If compatible, adaptor 17 and DMD 15 will be able to establish data communication channel 55, said step being represented by reference numeral 209. It should be noted that, upon establishing data communication channel 55 between adaptor 17 and DMD 15, adaptor microcontroller 65 simultaneously instructs indicator 85 to provide a signal (e.g., a solid, non-flashing green light) to notify the user of the established data communication channel.

With data communication channel 55 having been established between adaptor 17 and DMD 15, adaptor microcontroller 65 retrieves a first bundle of data from adaptor memory 69 and, in turn, sends said first bundle of data to wireless controller 73, as represented by reference numeral 211. It should be noted that the size of the first data bundle retrieved from adaptor memory 69 is dependent upon the transfer protocol established between adaptor 17 and DMD 15. In step 213, wireless controller 73 coverts the first bundle of received data into a format suitable for wireless transmission. The converted first bundle of data is then sent from wireless controller 73 to wireless transceiver 75 through transmission line TxD, said step being represented by reference numeral 215. In step 217, the converted first bundle of data is wirelessly transmitted from wireless transceiver 75 to DMD 15.

Having completed the transfer of the first bundle of data from adaptor 17 to DMD 15, microcontroller 65 then sends out a signal to determine whether additional data bundles remain in adaptor memory 69, said step being represented by reference numeral 219. If there are no additional bundles of data located in memory 69, the data transfer process between adaptor 17 and DMD 15 terminates, as represented by reference numeral 221. It should be noted that once method 201 reaches step 221, adaptor microcontroller 65 simultaneously turns off indicator 85 to notify the user that the transfer of data between adaptor 17 and DMD 15 has completed.

However, if additional bundles of data are located in memory 69, adaptor microcontroller 65 retrieves the next sequential bundle of data from adaptor memory 69 and, in turn, forwards said bundle to wireless controller 73, as represented by reference numeral 223. In step 225, wireless controller 73 coverts the next sequential bundle of received data into a format suitable for wireless transmission. The converted bundle of data is then sent from wireless controller 73 to wireless transceiver 75 through transmission line TxD, said step being represented by reference numeral 227. In step 229, the converted bundle of data is wirelessly transmitted from wireless transceiver 75 to wireless enabled DMD 15.

Having completed the transfer of the next sequential bundle of data from adaptor 17 to DMD 15, microcontroller 65 then sends an additional signal to determine whether more bundles of data remain in memory 69 for adaptor 17, said step being represented by reference numeral 231. If there are no additional bundles located in adaptor memory 69, method 201 proceeds to step 221. However, if additional bundles of data are located in adaptor memory 69, method 201 returns to step 223. As such, method 201 continues until all of the bundles of data stored in adaptor memory 69 are wirelessly transmitted to DMD 15.

As noted above, data communication device 61 of adaptor 17 is preferably in the form of a strip-type connective interface which includes multiple metal contacts and communication device 27 is preferably in the form of a slotted, multipurpose test port which includes multiple metal contacts. Preferably, the strip-type connective interface of device 27 is sized and shaped to be fittingly inserted into the slot of the multi-purpose test port of device 61 so that the metal contacts of device 61 are disposed in direct electrical contact with the metal contacts within device 27. In this manner, data communication channel 53 is established between ATI 13 and adaptor 17.

However, it is to be understood that system 11 is not limited to the particular type of electrical interconnection between ATI 13 and adaptor 17 as described above. In particular, system 11 is not limited to data communication device 61 being in the form of a strip-type connective interface with multiple metal contacts and data communication device 27 being in the form of a multi-purpose test port with multiple metal contacts. Rather, it is to be understood that data communication devices 27 and 61 are meant to represent any complementary pair of connectors which can be removably interconnected so as to establish a serial data communication channel therebetween.

Figure 9:
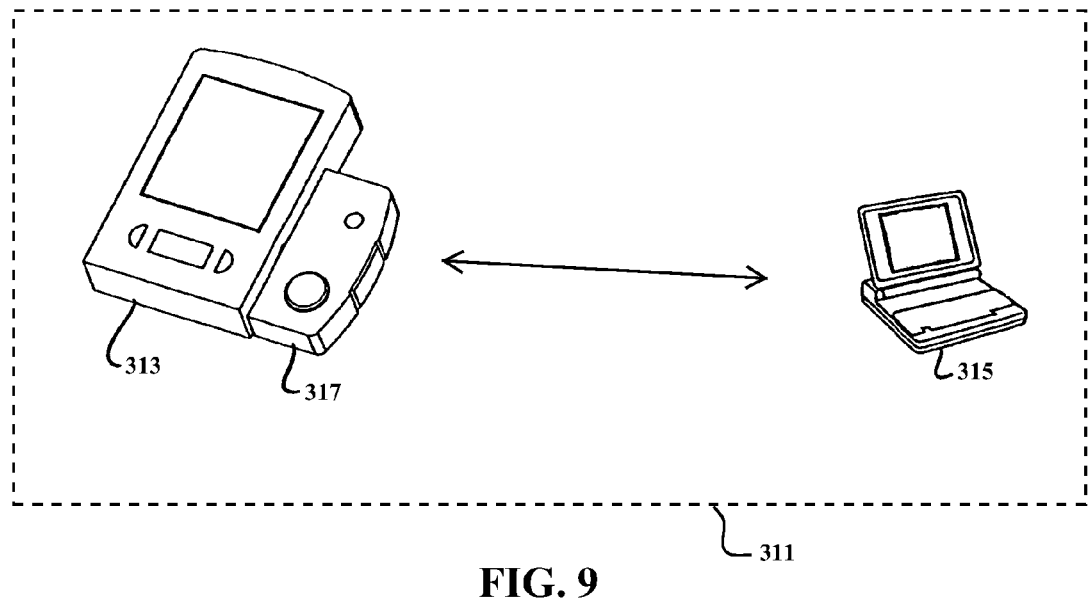
FIG. 9 is a perspective view of a second embodiment of a system for transferring analyte test data, said system being constructed according to the teachings of the present invention, the adaptor being shown connected to the analyte test instrument, the adaptor being shown in wireless communication with the data management device.

As an example, referring now to FIG. 9, there is shown a second embodiment of a system for transferring data, said system being constructed according to the teachings of the present invention and identified generally by reference numeral 311.

System 311 is similar to system 11 in that system 311 comprises an analyte test instrument (ATI) 313, a data management device (DMD) 315 and an adaptor 317, wherein analyte test data stored in ATI 313 can be wirelessly transmitted to DMD 315 via adaptor 317.

The principal distinction between system 311 and system 11 lies in the fact that adaptor 317 releasably interconnects with ATI 313 in a different manner in which adaptor 17 releasably interconnects with ATI 13. Specifically, ATI 313 comprises a data communication device 327 which is in the form of a conventional, female-type, conductive phone jack receptacle and adaptor 317 comprises a data communication device 361 which is in the form of conventional, male-type, conductive phone jack. Preferably, the phone jack receptacle of device 327 is sized and shaped to fittingly and releasably receive the phone jack of device 361, with device 361 being disposed in direct electrical contact with device 327. As such, a serial data communication path can be established between adaptor 317 and ATI 313, which is highly desirable.

It should be noted that the adaptors of the present invention which were described in detail above can be used in conjunction with various types of analyte test instruments. By providing adaptors which can be used with different types of analyte test instruments, the present invention serves to create a standardized means for wirelessly transmitting data of any format from any type of analyte test instrument to a common data management device, which is highly desirable.

The embodiments shown in the present invention are intended to be merely exemplary and those skilled in the art shall be able to make numerous variations and modifications to it without departing from the spirit of the present invention.

All such variations and modifications are intended to be within the scope of the present invention as defined in the appended claims.

What is claimed is:

1. A system for transferring data comprising:
   (a) an analyte test instrument which is adapted to store data, said analyte test instrument having a first data communication device, the first data communication device having a test port for receiving an analyte test strip;
   (b) an adaptor removably connected to said analyte test instrument, said adaptor being in data communication with said analyte test instrument through a first data communication channel, and
   (c) a data management device in data communication with said adaptor through a second data communication channel, said second data communication channel being a wireless data communication channel, said adaptor comprising:
      (1) a second data communication device;
      (2) a microcontroller in electrical connection with said second data communication device;
      (3) a wireless controller in electrical connection with said microcontroller; and
      (4) a wireless transceiver in electrical connection with said wireless controller, said wireless transceiver being adapted to wirelessly communicate with said data management device through the second data communication channel wherein, said adaptor further comprises:
         (i) memory in electrical connection with said microcontroller;
         (ii) a housing shaped to define an interior cavity; and
         (iii) a portion of the second data communication device extending out from the housing and capable of being removably received within the analyte test port of the first communication device so as to establish the first data communication channel between said adaptor and said analyte test instrument.

2. The system as claimed in claim 1 wherein the second data communication device is adapted to be electrically and mechanically connected to the data communication device of said analyte test instrument.

3. The system as claimed in claim 1 wherein the second data communication device includes a rectangular strip with one or more contact strips deposited thereon.

4. The system as claimed in claim 3 wherein the first data communication device includes at least one contact strip and is adapted to electrically and mechanically receive the second data communication device.

5. The system as claimed in claim 2 wherein said adaptor further comprises a power source electrically connected to said memory, said microcontroller, said wireless controller, and said wireless transceiver.

6. The system as claimed in claim 1 wherein said adaptor further comprises a power source electrically connected to said memory, said microcontroller, said wireless controller, and said wireless transceiver.

7. The system of claim 1, wherein the portion of the second data communication device comprises a substantially rectangular strip having a plurality of metal contact strips disposed thereon.

8. The system of claim 7, wherein the plurality of metal contact strips are disposed substantially along an entire length of the rectangular strip.

9. The system of claim 7, wherein the plurality of metal contact strips are spaced apart and generally parallel to each other.

10. The system of claim 1, wherein the portion of the second data communication device extends through a narrow slot in the housing.

11. The system of claim 1, wherein the adaptor further comprises:
   a user input device disposed within the interior cavity of said housing and in electrical connection with said microcontroller, said user input device at least partially projecting out through said housing, and
   an indicator disposed within the interior cavity of said housing and in electrical connection with said microcontroller, said indicator at least partially projecting out through said housing.

12. The system of claim 1, wherein the portion of the second data communication device has the approximate width and thickness of the analyte test strip.

13. A method for transferring data stored on an analyte test instrument to a data management device via an adaptor, said adaptor being independent from said analyte test instrument, comprising:
   (a) removably connecting said adaptor to a test port of an analyte test instrument to establish a first data communication channel between said adaptor and said analyte test instrument, the test port being configured to receive an analyte test strip when not connected to the adaptor;
   (b) transferring data stored on said analyte test instrument to said adaptor through the first data communication channel; and
   (c) transmitting the transferred data from said adaptor to said data management device through a second data communication channel, the second data communication channel being a wireless data communication channel, wherein said adaptor comprises:
      (1) a first data communication device;
      (2) a microcontroller in electrical connection with said first data communication device;
      (3) a wireless controller in electrical connection with said microcontroller; and
      (4) a wireless transceiver in electrical connection with said wireless controller, said wireless transceiver being adapted to wirelessly communication with said data management device through the second data communication channel, wherein said adaptor further comprises:
         (i) memory in electrical connection with said microcontroller;
         (ii) a housing shaped to device an interior cavity; and
         (iii) a portion of a second data communication device extending out from the housing and capable of being removably received within the analyte test port of the first data communication device so as to establish the first data communication channel between said adapter and said analyte test instrument.

14. An adaptor for communicating data between a data management device and an analyte test instrument having an analyte test port configured for receiving an analyte test strip, comprising:
   a housing shaped to define an interior cavity;
   a data communication device disposed within the interior cavity, a portion of the data communication device extending out from the housing and capable of being removably received within the analyte test port of the data communication device so as to establish a first data communication channel between said adaptor and said analyte test instrument;

a microcontroller electrically coupled to the data communication device and disposed within the interior cavity;

a wireless controller electrically coupled to the microcontroller and disposed within the interior cavity; and a wireless transceiver electrically coupled to the wireless controller and disposed within the interior cavity, the wireless transceiver being adapted to wirelessly communicate with the data management device so as to establish a second communication channel between the adaptor and the data management device.

15. The adaptor of claim 14, wherein the portion of the data communication device comprises a substantially rectangular strip having a plurality of metal contact strips disposed thereon.

16. The adaptor of claim 15, wherein the plurality of metal contact strips are disposed substantially along an entire length of the rectangular strip.

17. The adaptor of claim 15, wherein the plurality of metal contact strips are spaced apart and generally parallel to each other.

18. The adaptor of claim 14, wherein the portion of the data communication device extends through a narrow slot in the housing.

19. The adaptor of claim 14, wherein the adaptor further comprises:

a user input device disposed within the interior cavity of said housing and in electrical connection with said microcontroller, said user input device at least partially projecting out through said housing, and an indicator disposed within the interior cavity of said housing and in electrical connection with said microcontroller, said indicator at least partially projecting out through said housing.

* * * * *

UNITED STATES PATENT AND TRADEMARK OFFICE
CERTIFICATE OF CORRECTION

PATENT NO. : 7,587,287 B2  Page 1 of 1
APPLICATION NO. : 10/407695
DATED : September 8, 2009
INVENTOR(S) : Connolly et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 532 days.

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

Page 1 of 1

PATENT NO.       : 7,587,287 B2
APPLICATION NO.  : 10/407695
DATED            : September 8, 2009
INVENTOR(S)      : Brian Edmond Connolly et al.

Figure 10:
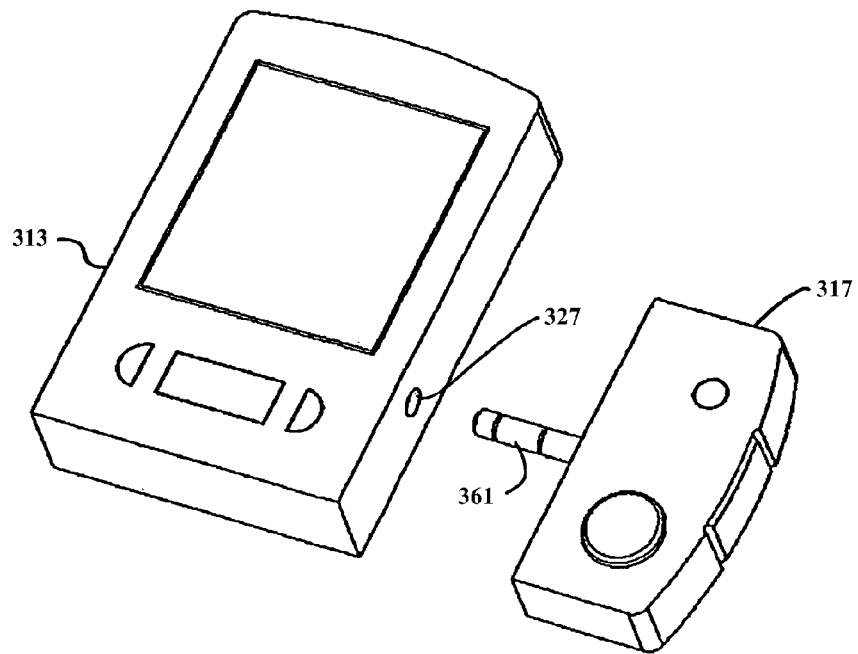
FIG. 10 is an enlarged front perspective view of the analyte test instrument and the adaptor shown in FIG. 9, the adaptor being shown disconnected from the analyte test instrument.

It is certified that error appears in the above-identified patent and that said Letters Patent is hereby corrected as shown below:

Specification:
Column 5, line 62, replace "to matingly receive" with --to fittingly receive--
Column 7, line 12, replace "a test strip is inserted" with --a test strip to be inserted--
Column 9, line 27, replace "is in is in" with --is in--
Column 10, lines 43-44, replace "sent by microncontroller" with --sent by microcontroller--
Column 10, line 62, replace "housing 17" with --housing 57--
Column 11, line 3, replace "Bluetooth, 802.11, Zigbee" with --Bluetooth®, 802.11, Zigbee®--
Column 11, line 33, replace "in is in the" with --in the--
Column 11, line 37, replace "indicator (e.g.," with --indicator 85 (e.g.,--
Column 11, line 66, replace "between ATI and" with --between ATI 13 and--
Column 12, line 59, replace "from ATI to DMD" with --from ATI 13 to DMD--
Column 13, line 33, replace "coverts" with --converts--
Column 13, line 56, replace "coverts" with --converts--
Column 14, line 12, replace "device 27 is" with --device 61 is--
Column 14, line 14, replace "test port of device 61" with --test port of device 27--
Column 14, line 44, replace "Specifically, ATI" with --Specifically, as shown in FIG. 10, ATI--

Claims:
Column 15, line 14 (Claim 1, line 9) replace "channel," with --channel;--
Column 15, line 36 (Claim 1, line 31) replace "the analyte test" with --the test--
Column 15, line 43 (Claim 2, line 3) replace "the data" with --the first data--
Column 15, line 45 (Claim 3, line 1) replace "claim 1" with --claim 2--
Column 15, line 67 (Claim 8, line 3) replace "the rectangular" with --the substantially rectangular--
Column 16, line 12 (Claim 11, line 6) replace "housing," with --housing;--
Column 16, line 45 (Claim 13, line 25) replace "communication" with --communicate--
Column 16, line 51 (Claim 13, line 31) replace "device" with --define--
Column 16, line 54 (Claim 13, line 34) replace "the analyte test" with --the test--
Column 17, line 20 (Claim 16, line 3) replace "the rectangular" with --the substantially rectangular--
Column 18, line 13 (Claim 19, line 6) replace "housing," with --housing;--

Signed and Sealed this
Twentieth Day of May, 2014

Michelle K. Lee
*Deputy Director of the United States Patent and Trademark Office*